United States Patent [19]
Rulf et al.

[11] Patent Number: 4,674,323
[45] Date of Patent: Jun. 23, 1987

[54] SELF-DIAGNOSTIC GEL PERMEATION/SIZE EXCLUSION CHROMATOGRAPH

[75] Inventors: Donald C. Rulf; Edwin R. North, both of Midland, Mich.

[73] Assignee: The Dow Chemical Company, Midland, Mich.

[21] Appl. No.: 761,076

[22] Filed: Jul. 31, 1985

[51] Int. Cl.$^4$ .......................................... G01N 30/88
[52] U.S. Cl. ................................ 73/61.1 C; 364/497; 422/70
[58] Field of Search ..................... 73/61.1 C; 364/497, 364/571; 210/635, 656, 198.2; 422/70

[56]   References Cited
U.S. PATENT DOCUMENTS

| | | |
|---|---|---|
| 3,954,617 | 5/1976 | Ishimatsu . |
| 3,962,206 | 6/1976 | Butler . |
| 4,042,499 | 8/1977 | Ramstad et al. . |
| 4,098,592 | 7/1978 | Prescott et al. . |
| 4,116,046 | 9/1978 | Stein ................................ 73/61.1 C |
| 4,118,316 | 10/1973 | Tally et al. . |
| 4,133,767 | 1/1979 | Bakalyar et al. . |
| 4,158,630 | 6/1979 | Stearns . |
| 4,217,223 | 8/1980 | Baba et al. . |
| 4,258,564 | 3/1981 | Hulme et al. ..................... 73/61.1 C |
| 4,267,054 | 5/1981 | Yoritomi et al. ..................... 210/659 |
| 4,271,697 | 1/1981 | Mowery, Jr. ..................... 73/61.1 C |
| 4,274,967 | 6/1981 | Snyder . |
| 4,315,754 | 2/1982 | Ruzicka et al. . |
| 4,338,404 | 6/1982 | Tanaka et al. . |
| 4,347,131 | 8/1982 | Brownlee ............................ 210/101 |
| 4,357,668 | 11/1982 | Schwartz et al. ..................... 364/497 |
| 4,364,263 | 12/1982 | Sankoorikal et al. ............. 73/61.1 C |
| 4,389,316 | 6/1983 | Falk ...................................... 210/656 |
| 4,404,845 | 9/1983 | Schrenker ........................ 422/70 X |
| 4,468,331 | 8/1984 | Antle et al. ........................ 210/659 |
| 4,468,742 | 8/1984 | Jenden et al. ....................... 364/497 |
| 4,500,432 | 2/1985 | Poole et al. ........................ 210/659 |
| 4,524,420 | 6/1985 | Glodo et al. ........................ 364/497 |
| 4,546,643 | 10/1985 | Bonneyrat et al. ............. 73/61.1 C |

OTHER PUBLICATIONS

NiKelly, J. G. et al. *Pulse Dampener for High Press–Liquid Chromat.* In Analy. Chem., vol. 51 (9), pp. 1585–1588, Aug. 1979.

Mills, A. D. et al. *An Automated System for Chromatogrphic Analysis*, In Philips Res. Lab. Annual Rev. (G.B.) pp. 38–40, 1978.

Paper entitled "Modern Size–Exclusion Liquid Chromatography" by W. W. Yau, J. J. Kirkland and D. D. Bly, 1979, Index and pp. 38–42.

Advances in Instrumentation, vol. 35, Part 2, Proceedings of the ISA Conference and Exhibit, Oct., 1980, authored by R. A. Mowery, Jr. brochure entitled HP 1090 GPC System, by Hewlett Packard.

Article entitled "On–Line Process Size–Exclusion Chromatogrphy" by R. A. Mowery, Jr., En. N. Fuller and R. K. Bade, reprinted from American Laboratory, May, 1982.

Brochure entitled "OPTICHROM 2100 Process Chromatograph System" of Applied Automation, Inc.

Article entitled "Water Systems for Liquid and Gel Permeation Chromatography".

Brochure entitled "The Waters 840".

Article entitled "Gel Permeation Analyzes Polymers", C & EN, Dec. 17, 1962.

"Gel Permeation Chromatography, I. A New Method for Molecular Weight Distribution of High Polymers" from Journal of Polymer Scient: Part A, vol. 2, pp. 835–843, 1964.

*Primary Examiner*—Stewart J. Levy
*Assistant Examiner*—Joseph W. Roskos

[57]   ABSTRACT

A SEC/GPC chromatograph which includes columns for fractionating polymers samples by molecular weight, conveying apparatus for causing a stream of solvent to flow through the columns from a source of this solvent, a rotary injection valve for sequentially injecting a series of polymer samples into the solvent stream ahead of the columns, a detector for generating a peak signal indicative of the molecular weight of the fractionated polymer samples eluting from the columns and a computer controller for processing the peak signal from the detector into a molecular weight distribution output, and for controlling the valve, and for performing several self-diagnostic tests.

15 Claims, 18 Drawing Figures

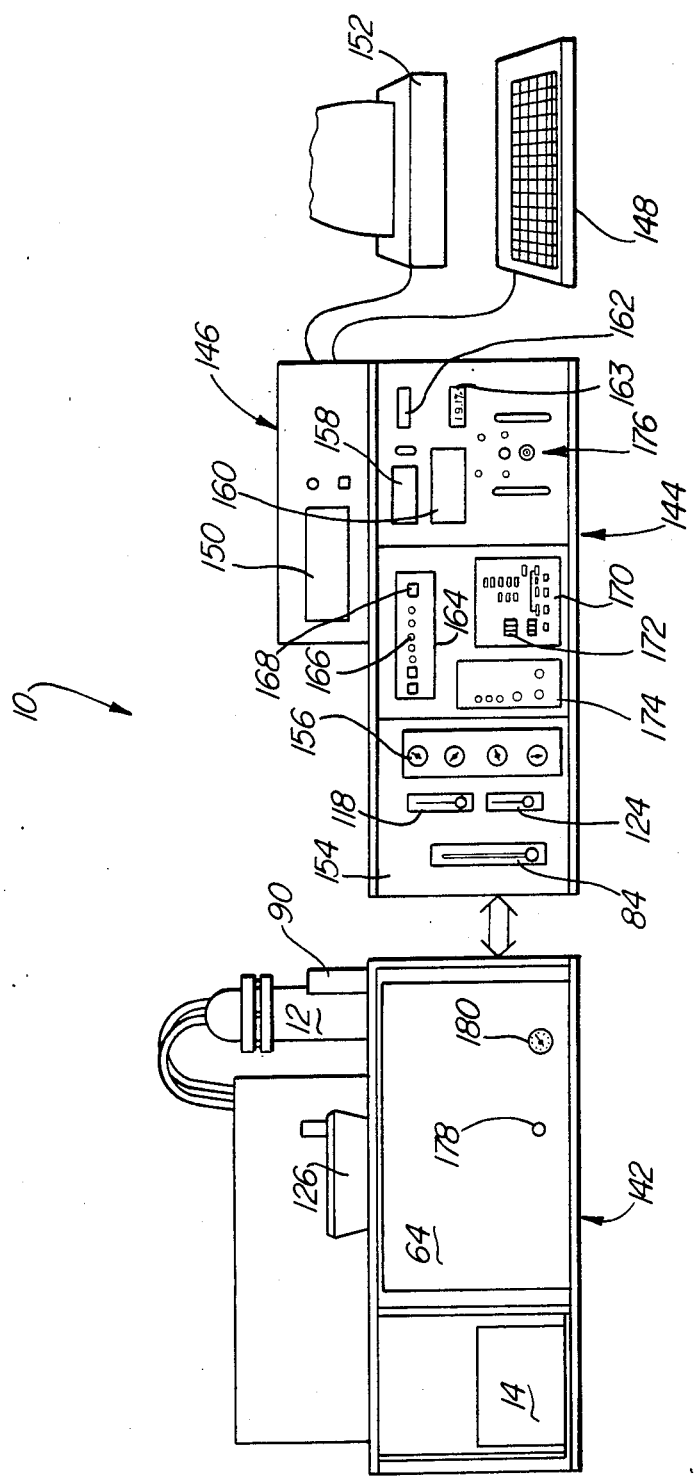

$$S = \left[ \sum_{i=1}^{n} \frac{\Delta x_i^2}{(n-1)} \right]^{1/2}$$

SELF-DIAGNOSTIC GEL PERMEATION/SIZE EXCLUSION CHROMATOGRAPH

BACKGROUND OF THE INVENTION

The present invention relates generally to the field of liquid chromatography, and relates particularly to a self-diagnostic gel permeation/size-exclusion chromatograph and method for determining the molecular weights and molecular weight distribution of polymers.

Polymers such as polystyrene and saran resins comprise a wide distribution of molecular size/molecular weights. The weight/size distribution for a particular polymer typically has a characteristic shape. Accordingly, one important way of controlling the properties of a polymer is to control the shape of its molecular weight/size distribution.

In view of the above, there is a present and growing need to generate routine molecular weight/size information in polymer production plants and laboratories. However, in order for this information to be meaningful, it must be sufficiently accurate to permit comparison with similar information generated by other polymer production plants.

The type of chromatograph which is capable of generating molecular weight/size distributions for polymers is generally referred to as a size-exclusion chromatograph (SEC) or a gel permeation chromatograph (GPC). While these terms are not precisely synonymous, they are both commonly used to describe the same chromatographic technique. To simplify the language below, these chromatographs will generally be referred to as SEC/GPC chromatographs. While there are several commercially available SEC/GPC chromatographs, these instruments have generally been designed with the assumption that the principal users will be chromatographers who possess the needed skills and experience to generate accurate results. As well known in the art, special skills and experience are needed to both correctly perform SEC/GPC measurements, and to correctly interpret the data generated. These commercial instruments also lack the diagnostics generally necessary for reliable, full-time operation outside of a research laboratory.

Accordingly, it is a principal object of the present invention to provide an SEC/GPC chromatograph which does not require any particular chromatographic expertise to successfully and reliably produce precise and molecular weight/size information in the field.

It is another object of the present invention to provide an SEC/GPC chromatograph which assures compatibility with the data generated by similar chromatographs located in other polymer production plants.

It is an additional object of the present invention to provide an SEC/GPC chromatograph which incorporates several self-diagnostic features that eliminate the need for an experienced chromatographic practitioner to operate the instrument and permit semi-automated operation.

It is yet another object of the present invention to provide an SEC/GPC chromatograph which is capable of substantially decreasing the test time required to analyze a series of polymer samples.

It is yet another object of the present invention to provide an SEC/GPC chromatograph which has the capability of refilling the eluant or solvent reservoir within the chromatograph by remote control. A convenient way of measuring the eluant liquid level within the chromatograph reservoir is also provided.

It is yet a further object of the present invention to provide an improved oven construction for a SEC/GPC chromatograph which permits convenient adjustment of the detector optical zero response.

It is still another object of the present invention to provide a SEC/GPC chromatograph which will automatically revert to a controlled shut down mode or a recycle mode when predetermined malfunctions have been detected.

It is a still further object of the present invention to provide a rugged SEC/GPC chromatograph which is capable of producing long term reproducible results.

SUMMARY OF THE INVENTION

To achieve the foregoing objectives, the present invention provides an SEC/GPC chromatograph which generally includes column means for fractionating polymer samples by molecular size, and conveying means for causing a stream of solvent to flow through the column means from a source of this solvent. Rotary injection valve means is provided for sequentially injecting a series of polymer samples into the solvent stream of the conveying means before the column means. Detector means is connected to the conveying means at the output of the column means for generating a peak signal indicative of the molecular weight of the fractionated polymer samples eluting from the column means. Controller means is provided for processing the peak signal from the detector means into a molecular weight distribution output, and for controlling the valve means such that a subsequent polymer sample is injected into the solvent stream before a prior polymer sample has completely eluted from the column means without interrupting the flow of the solvent stream.

In one form of the present invention, the controller means is a computer which is programmed to include several self-diagnostic features. These self-diagnostic features include various checks on the baseline without the computer having to know ahead of time what the baseline limits are for a particular polymer sample. Nor does the operator have to define these limits, as the baseline is defined automatically by the computer for each chromatogram as it processes the data. Another feature is the storage of the molecular weight distribution characteristics for a standard calibration sample in the memory of the computer controller. This is to permit a comparison of the memorized calibration sample with an identical calibration sample loaded by the technician as the first sample to be analyzed. If a sufficiently good match between these calibration samples does not occur, the computer controller will generate an error message which will be displayed to warn the operator of a problem, such as a change in the characteristics of the columns.

Additional advantages and features of the present invention will become apparent from a reading of the detailed description of the preferred embodiment which make reference to the following set of drawings in which:

BRIEF DESCRIPTION OF THE DRAWINGS

FIG. 2 is a front elevation view of the SEC/GPC chromatograph illustrated in FIG. 1.

DETAILED DESCRIPTION OF THE PREFERRED EMBODIMENT

Figure 1A:
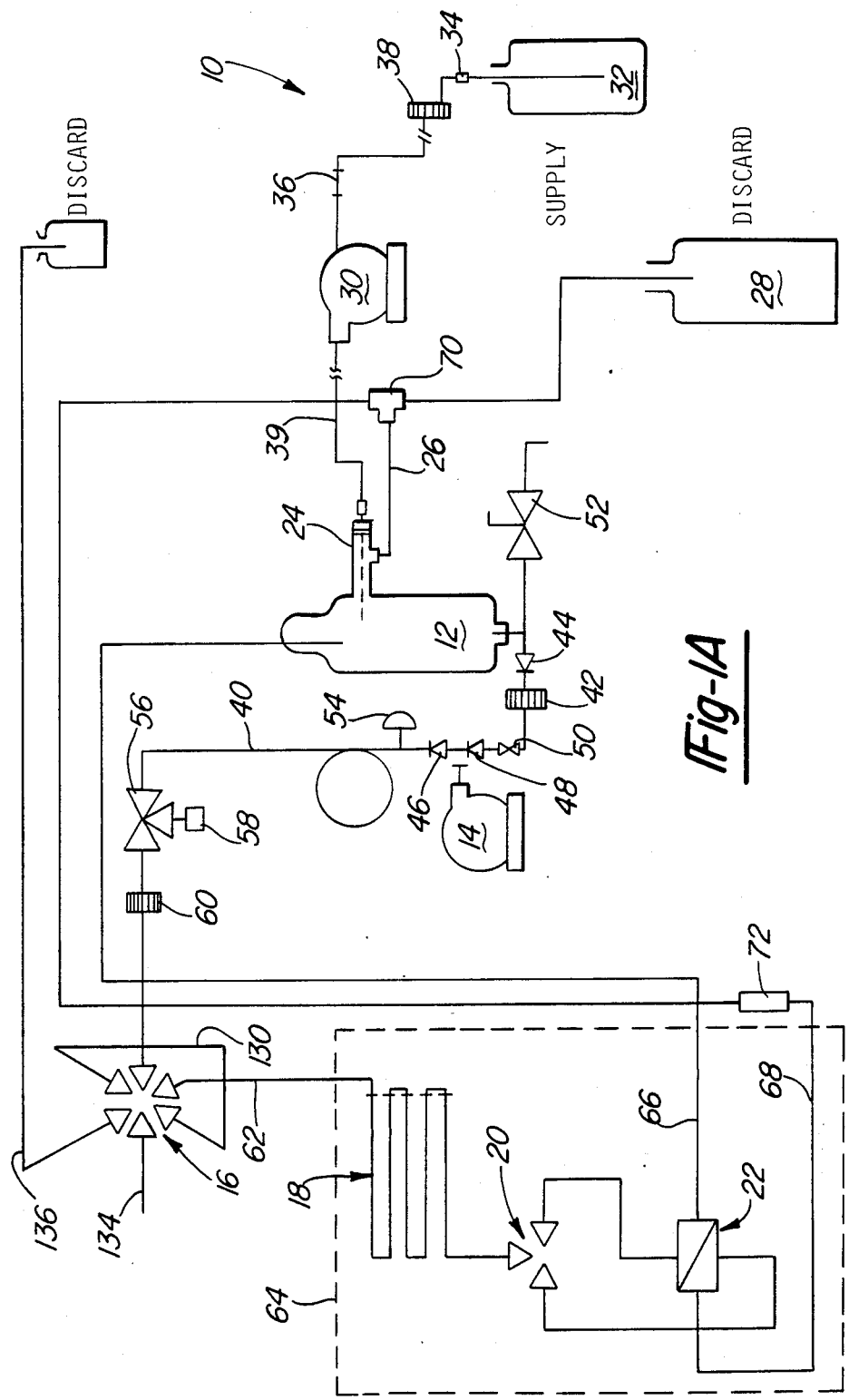
FIGS. 1A–1C are schematic diagrams of a SEC/GPC chromatograph according to the present invention.

Referring to FIG. 1A, a schematic diagram of the solvent and sample delivery sub-system for a SEC/GPC chromatograph 10 according to the present invention is shown. This sub-system for the chromatograph 10 generally comprises a reservoir 12, a pump 14, a sample injection valve 16, a set of, e.g., five columns 18 which are connected in a series, a switching valve assembly 20, and detector 22. The reservoir 12 is used to contain a supply of a suitable solvent or eluant, such as tetrahydrofuran (THF). The reservoir 12 is constructed of a copper-plated stainless steel tank which is formed with a side port 24. The radially extending side port 24 is used to prevent the reservoir 12 from being overfilled. Accordingly, a discharge conduit 26 is connected to the output port 24 to permit excess solvent from the reservoir 12 to be transmitted to a discharge vessel 28 at atmospheric pressure.

The side port 24 is also provided with a connection to a refill pump 30 which is adapted to pump solvent to the reservoir 12 from a suitable source, such as supply vessel 32. A quick connect coupling 34 is used to provide a releasable connection between the supply conduit 36 and the supply vessel 32. A filter 38 may also be provided in the supply conduit 36. As shown in FIG. 1A, the supply conduit 39 from the refill pump 30 preferably extends well into the side port 24 of the reservoir 12 to facilitate the delivery of solvent delivery into the main tank body of the reservoir 12.

It should be appreciated that the solvent refill components described above enable the reservoir 12 to be refilled by remote control. As will be more fully discussed below, a switch is mounted to the front panel of the chromatograph dry unit for controlling the refill pump 30. With the solvent supply vessel 32 and/or the refill pump 30 contained in an atmosphere controlled or ventilated hood, the operator may refill the reservoir 12 from the remotely located dry unit for the chromatograph 10 and thereby avoid exposure to the solvent.

It should also be appreciated that the vertical position of the side port 24 will control the height of the solvent height liquid level within the reservoir 12, and the position of the side port 24 may be varied in accordance with the appropriate application. Thus, for example, it may be desirable to provide such a port in the top cap for the reservoir 12 when it is appropriate to minimize the gas space in the reservoir.

In one form of the present invention, the quick connect coupling 34 is a Swagelock SSQM connector, the filter 36 is a Nupro SS2DF2 filter, and the refill pump 30 is a Fluorocarbon SPM100 pump. However, it should be understood that these components are identified for exemplary purposes, and that other suitable components may be used in the appropriate application. As will be more fully appreciated below, the principals of the present invention are not limited to any particular component model or type used in the chromatograph 10. For example, while it is preferred that the conduits (eg. 26, 36, 39) be made out of stainless steel or copper when THF is used as a solvent, other suitable conduit constructions can be employed for other types of solvents.

The main outlet or discharge port of the reservoir 12 is connected to the pump 14 through a conduit path 40 which includes a filter 42, check valves 44–48, and a cutoff valve 50. Another cutoff valve 52 is connected directly to the main output or discharge port of the reservoir 12 to permit the reservoir 12 to be drained and periodically flushed by the operator. The valve 50 is used to shut off the supply of solvent from the reservoir 12 when it is desired to do maintenance work on the pump 14. In one embodiment according to the present invention, the valves 50 and 52 are Whitey Model SS4152 ball valves. The pump 14 may be any suitable pump, such as a dual piston positive displacement pump. Examples of suitable pumps are the Hewlett Packard 1081B pump, and the Waters 510 pump. It should be noted that in some of these pump models, the check valves 46 and 48 come constructed with the pump. A pressure transducer 54 is also provided in the conduit path 40 to measure the pressure at the outlet side of the pump 14. As noted above for the inlet/outlet check valves 46–48, the pressure transducer 54 is a standard feature in some pump construction.

The pump 14 provides a steady stream of solvent flow (eg., 0.1 ml./min.) through the conduit path 40 from the reservoir 12. The conduit path 40 is provided with a loop to act as a flow restrictor which will dampen out pressure pulses produced by the pump 14. A manually actuated three-way valve 56 is provided in the conduit path 40 to permit air bubbles to be drawn out of the conduit line after assembly or maintenance. The three-way valve 56 is also used as a means of relieving pressure in the line between the pump 14 and the columns 18, so that the pump can be easily primed during system start-up. A Luer fitting 58 may be connected to the vent port of the three-way valve 56. This will permit a syringe to be connected to the valve 56 to enable the presence of air bubbles to be observed in the syringe when solvent is pumped into this syringe through the conduit path 40 at reduced pressure. Downstream from the three-way valve 56 is a high pressure filter 60. The high pressure filter 60 is the last filter that the solvent sees before it enters the columns 18. In one form of the present invention, the three-way valve 56 is a Nupro Model SSI020183 valve, and the filter is a Hewlett Packard Model 79114-62701 filter.

Immediately downstream from the filter 60 is the injection valve 16. The injection valve 16 forms part of an automatic sample changer which will be discussed in connection with FIG. 4. However, suffice it to say at this point that the injection valve 16 is adapted to inject a polymer sample into the solvent stream leading to the columns 18. The injection valve 16 is connected to the columns 18 via a conduit 62 which extends through the walls of an oven 64. The columns 18, the switching valve 20, and the detector 22 are all contained in the oven 64 in order to provide stable temperature control of these components. In one form of the present invention, the detector 22 is also thermally protected by being enclosed in a thick brass box which is lined with fiberglass insulation. This thermal protection, plus the temperature control provided by the oven, enhances the quality of the detector's baseline signal.

The columns 18 are shown to comprise a set of five individual columns connected in series. While not readily discernible from FIG. 1A, it is preferred that the flow system dead-volume between the injection valve 16 and the detector 22 be minimized. In one form of the present invention, the oven 64 and its temperature controller comprise a Combustion Engineering Model 007 oven unit, the detector is a Waters Model R401 refractometer, and the columns 18 are Toyo Soda Model TSK GMH6 columns. Again, as noted above, these particular components may be replaced with other suitable components, such as an ultraviolet light type detector. Thus, while it is preferred that the columns be provided with a linear sample retention range, any suitable columns for fractionating the polymer samples of interest by molecular weight/size may be employed. Similarly, any suitable detector means may be employed which will generate a peak signal which is indicative of the molecular weight/size of the fractionated polymer sample eluting from the columns.

The switching valve assembly 20 is used to switch between the reference and analytical sides of the detector 22. This provision for changing the flow path between the reference and analytical sides of the detector 22 is advantageous, because it permits the reference side of the detector to be refreshed automatically during normal operation of the chromatograph 10. This is in contrast to prior SEC/GPC chromatographs in which the solvent on the reference side of the detector has to be manually replaced by the operator. In accordance with the present invention, the computer controller for the chromatograph 10 will control the switching valve assembly 20 such that the solvent flow is diverted through the reference side of the detector 22 before a sample is to be injected into the chromatograph for analysis. Then, when samples are to be introduced into the chromatograph 10 for analysis, the controller will actuate the switching valve assembly 20, so that the flow is then diverted through the sample or analytical side of the detector 22. This will trap a quantity of solvent in the reference side of the detector 22, and thereby assure that this solvent is fresh and that this trapped solvent represents the same solvent to be used in transporting the sample through the columns 18 and the detector 22.

The outlet port for the reference side of the detector 22 is connected to a conduit 66 which leads back to the reservoir 12. Accordingly, it should be appreciated that when the switching valve assembly 20 diverts the solvent flow to the reference side of the detector 22, a recirculation loop is created between the reservoir 12, the pump 14, the injection valve 16, the columns 18, the switching valve 20, and the detector 22. This recirculation loop permits the solvent from the reservoir 12 to be conserved by automatically recycling the solvent stream back to the reservoir. One of the advantages of this recirculation loop is that it permits the chromatograph 10 to operate for a long period of time following a start-up without wasting any of the solvent. As will be appreciated by those skilled in the art, this long period of time will facilitate the stabilization of the temperatures and flow rates to preferred equilibrium values.

A conduit 68 is connected to the outlet port of the analytical side for the detector 22. The conduit 68 leads to the discard vessel 28 through a T-fitting 70 which is connected to conduit 26. This flow path to discard is provided when samples are to be introduced into the chromatograph 10. A thermo-pulse flow meter 70 is provided in the discard flow path 68 to measure the flow rate of the sample stream during the sample run mode for the chromatograph 10. In one form of the present invention, the flow meter 70 is a Molytek Thermo-Pulse flow meter. While thermo-pulse flow meters are preferred due to the low flow rate of the solvent (eg., 0.1 ml. per minute), other suitable flow meters may be used in the appropriate application.

Figure 1B:
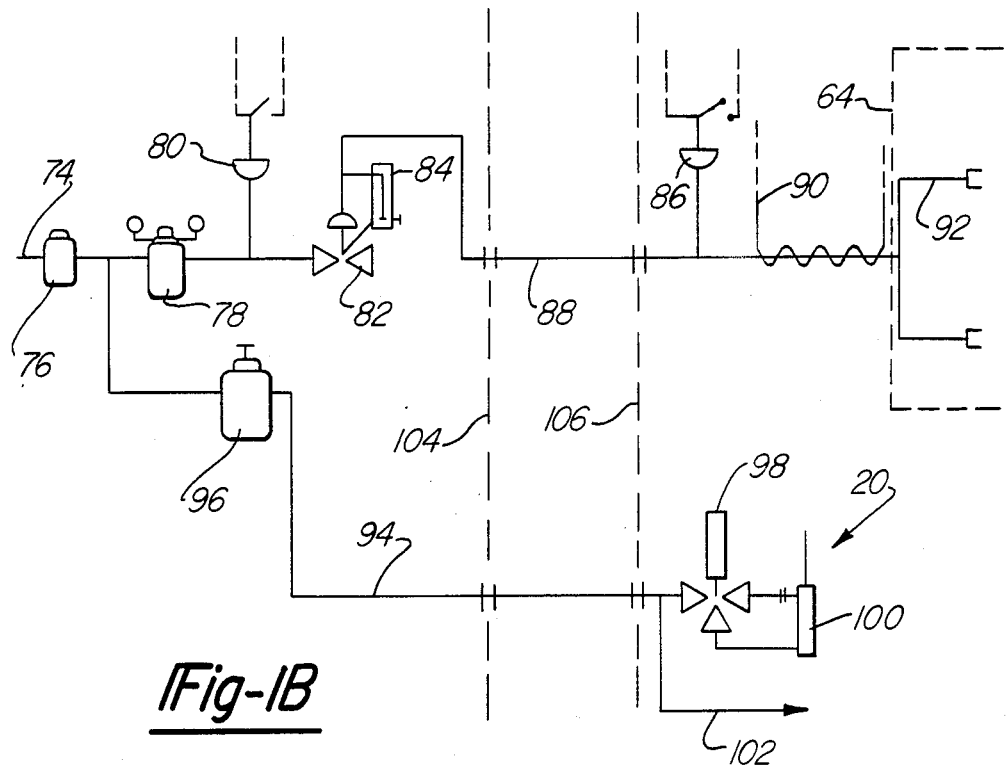

Referring to FIG. 1B, a schematic diagram of the air distribution sub-system for the chromatograph 10 is shown. As will be discussed below, air is used to control the temperature of the oven 64, and to operate the switching valve assembly 20 and the automatic sample changer. Air flow from a suitable supply source is conveyed through a conduit 74 to a filter 76. The outlet from the filter 76 is divided into two flow paths. The first flow path is directed to the oven 64 while the second flow path is directed to the switching valve assembly 20. The first flow path includes a pressure regulator 78, a pressure switch 80, a pressure regulator valve 82, a flow meter 84, and a flow switch 86. This oven air flow path 88 is also provided with a tubular resistance heater 90, and a manifold 92 within the oven 64 for distributing the air throughout the oven's interior. The heated air provides both a high degree of temperature control, and a constant purge of the oven's atmosphere.

The pressure switch 80 and the air flow switch 86 are used as redundant controls to sense for the pressure of a malfunction in the air flow to the oven 64. These two switches provide signals to the computer controller for the chromatograph 10, which will operate to disable the oven heater 90 in the event of a decrease in the air flow rate below a predetermined threshold or a decrease in the air flow pressure below a predetermined threshold. A high air flow rate (eg., 100 cu. ft. per hour) is preferred in order to provide rapid replacement of the atmosphere within the oven 64, so as to minimize any safety hazard resulting from any possible leak in the solvent line which could occur.

The air flow path 94 to the switching valve assembly 20 includes a pressure regulator 96, for regulating the pressure to the pneumatically operated solenoid valve 98 of the switching valve assembly 20. The switching valve assembly also includes a three-port switching valve 100, which is connected to the solenoid valve 98. In one form of the present invention, the solenoid valve 98 is a Clippard Model R481 four-way valve, while the switching valve 100 is a Valco Model C34 switching valve. It should also be noted that a conduit 102 is connected to the conduit 94 to permit an air flow path to the auto sampler assembly shown in FIG. 4.

The two dashed lines 104 and 106 represent the dividing lines for the dry and wet units respectively for the chromatograph 10. All the components to the left of the dashed line 104 are contained in the dry unit of the chromatograph 10, while all of the components to the right of the dashed line 106 are contained in the wet unit of the chromatograph. In one form of the present invention, the filter 76 is a Balston Type 92BX filter, the regulator 78 is a Balston Type 92BX pressure regulator, the pressure switch 80 is a Whitman Controls Model P/N 117G-10N-C12L-X switch, the pressure regulator 82 is a Conoflow Model H-21 regulator, the flow switch 86 is a Flotect Model D-6 Loflow Dwyer flow switch, and the regulator 96 is a Balston Type 93A pressure regulator.

Figure 1C:
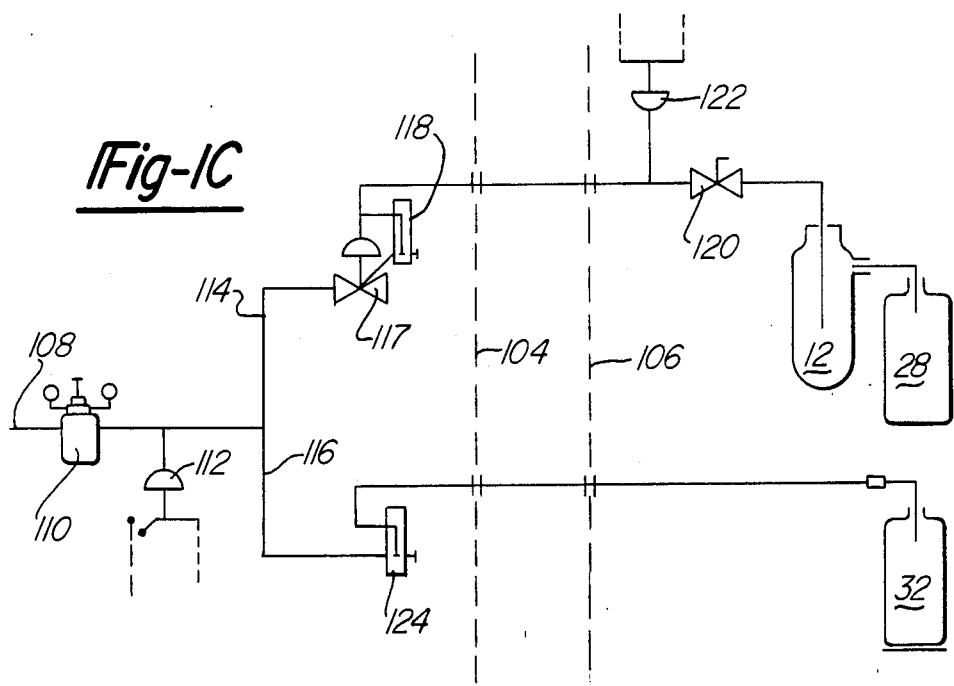

Referring to FIG. 1C, a schematic diagram for the helium distribution sub-system for the chromatograph 10 is shown. Helium is used in the chromatograph 10 as a purge gas to eliminate oxygen in the reservoir 10 and the solvent supply vessel 32. The use of helium gas also provides a convenient way of measuring the solvent liquid level in the reservoir 12, as will be described below. While helium gas is preferred, it should be understood that other suitable gasses may be used in the appropriate application.

A conduit 108 is connected to a source of helium gas. A pressure regulator 110 and a pressure switch 112 are included in the conduit flow path 108. The pressure switch 112 is used to provide a signal to the computer controller for the chromatograph 10 which will indicate if the helium pressure in the conduit 108 has fallen below a predetermined threshold level. In such an event, the computer controller will operate to prevent the injection of any further samples into the chromatograph 10.

Downstream from the pressure switch 112, the flow path 108 is divided into a flow path 112 to the reservoir 12 and the flow path 116 to the solvent supply vessel 32. The flow path 114 is provided with a pressure regulator 116 which sets the helium flow rate to the reservoir 12 (eg., 10-20 cc/min.) and a flow meter 118. A shut off valve 120 is provided for maintenance purposes and a differential pressure cell 122 is provided for measuring the solvent liquid level within the reservoir 12. The differential pressure cell 122 operates as a dip tube sensor which will generate a signal indicative of the back pressure on the helium gas produced by the solvent liquid level in the reservoir 12. This signal may be converted in the computer controller for the chromatograph 10 into a signal which is calibrated to the height of the liquid level within the reservoir 12.

The conduit flow path 116 is provided with a manually readable flow meter 124. Both the flow meters 118 and 124 may be mounted to the front panel of the dry unit for the chromatograph 10 in order to provide the operator with a visual indication of the flow rates through these conduit paths. In one form of the present invention, the differential pressure cell 122 is a Dwyer Model 601-6 cell, and the remaining components are similar to those illustrated in the air distribution sub-system of FIG. 1B.

Figure 4:
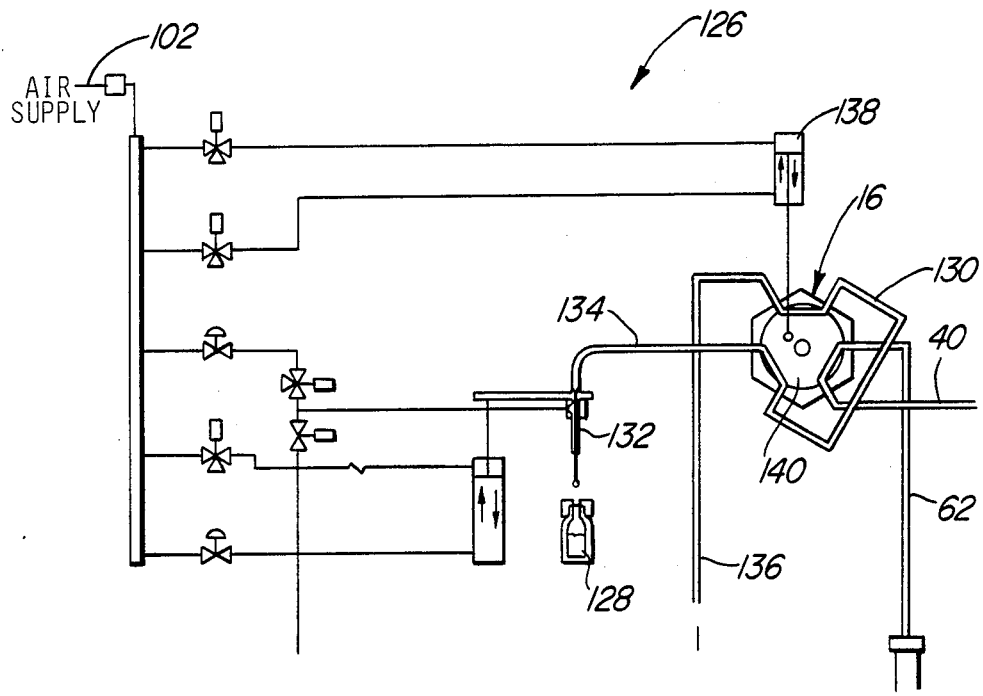
FIG. 4 is a schematic diagram of the automatic sampler changer illustrated in FIG. 1A.

Referring to FIG. 4, a schematic diagram of the automatic sample changer assembly 126 is shown. The particular sample changer assembly illustrated is a Varian Model 8000 Auto Sampler, which includes the injection valve assembly 16. The sample changer 126 is operated pneumatically under the control of electrical signals from its control module. The control module for the sample changer 126 is located in the dry unit of the chromatograph 10, and is subject to the supervision of the computer controller for the chromatograph 10.

The samples for analysis are contained in small glass vials 128. These vials are sealed with screwed-on plastic caps and multi-layered septa. The septa are composites of Teflon (a Dupont trademark) plastic and silicone rubber. The sample is delivered from the vial 128 to the sample loop 130 by air pressure via a concentric double needle 132 which enters the sample vial 128 through the multi-layered septum. The air passing into the vial 128 through the outer needle pressures the headspace in the vial, and forces liquid out of the vial through the inner needle. This liquid is then transmitted through the conduit 134 to the sample loop 130. A discharge conduit 136 is connected to the outlet of the sample loop 130 to permit disposal of the excess or unneeded liquid from the sample vial 128.

The sample changer 126 is provided with a two-position pneumatic cylinder 138 which is used to alternatively connect the sample loop 130 to the high pressure solvent supply conduit 40 or the disposal conduit 126. With this type of rotary injection valve, the sample may be loaded into the sample loop at low pressure without disturbing the solvent flow to the columns 18. Then, when it is desired to inject the sample into the solvent stream, the pneumatic cylinder 138 is actuated to quickly rotate the circular rotor 140 of the injection valve 16 by 60 degrees to connect the sample loop 130 to the high pressure solvent supply conduit 40. Sometime following the transmittal of the polymer sample in sample loop 130 through the conduit 62, the pneumatic cylinder 138 may be actuated to return to its initial position, so that another sample may be loaded into the sample loop. The sample changer 126 may then be indexed to place the next vial 128 to the carousel under the pressurizing needle assembly 132. In order to fully flush the sample loop 130, it is desirable to minimize the flow path internal volume leading to the sample loop from the vial 128. Accordingly, before the samples are placed in the vials, it is preferred that they be filtered to prevent plugging at this conduit path.

Referring to FIG. 2, a front elevation view of the chromatograph 10 is shown. The chromatograph 10 for safety enhancement is generally comprised of a wet unit 142, a dry unit 144, and a computer 146 which is shown to be located on top of the dry unit 144. The computer 146 forms part of the computer controller circuit for the chromatograph 10 which will be discussed in connection with with FIG. 3. A keyboard 148 is connected to the computer 146 to permit the operator to enter information such as the identification of each of the samples in the carousel for the sample changer 146. A cathode ray tube 150 is provided to permit a visually perceptible display of input information, menus, data, and results. Similarly, a printer 152 is connected to the computer 146 to permit a hard copy of the analytical results to be made, such as a chromatogram illustrating the molecular weight distribution for the sample analyzed by the chromatograph 10.

The front panel 154 of the dry unit 144 is shown to include several controls and readout devices. For example, the front panel 154 includes the flow meters, 84, 118, and 124. Similarly, the front panel 154 is provided with a number of pressure gauges 156 to provide a visual indication of the helium and air supply lines both before and after the regulators. A light emitting diode (LED) display 158 provides a visual indication of the peak signal voltage output from the detector 22, while the LED display 160 provides a visual indication of the temperature of the detector. Any suitable temperature sensor may be employed to provide a reading of the detector temperature, such as a thermistor embedded into the detector housing. A, preferably, LED display 162 is also provided to give the operator a visual indication of the solvent liquid level within the reservoir 12.

A, preferably, LED display 163 is used to give a visual indication of the outlet pressure of the pump 14. A sub-panel 164 provides a number of lights 166 which indicate the operating mode that the chromatograph 10 is currently in. For example, one of these lights would be used to indicate a recycle mode, while another of these lights would be used to indicate a sample run mode. The panel 164 is also provided with a switch 128 which controls the refill pump 30.

A control module 170 for the sample changer 126 is also mounted to the front panel 154 of the dry unit 144. The control module 170 is provided with various controls for the operation of the sample changer 126, such as a thumbwheel switch 172 which displays the time period between sample injections. An intelligent data collection device 174 is also mounted to the front panel 154 of the dry unit 144. The device 174 is used to collect peak signal data from the detector 22 under supervisory commands from the computer 146. The device 174 also converts the analog peak signal data to a digital form. In one form of the present invention, the intelligent data collection device 174 is a Nelson Analytical Series 861 computer interface. However, it should be appreciated that the computer 146 may be suitably constructed to directly collect data from the detector 22 in the appropriate application. The dry unit 144 is also provided with suitable controls 176 for the thermal pulse flow meter 72.

As shown in the front door of the oven 74 of the wet unit 142, a manually actuated device 178 is provided to adjust the zero point or base line response of the detector 22. The device 178 comprises a spring-loaded rotatable rod which extends through the door of the oven 64. The spring-loaded rod is formed with a gear at the end which is complimentary in shape to a gear connected to the sensitivity adjustment for the detector 22. This permits the operator to adjust the baseline zero adjustment of the detector 22 by simply depressing the control knob of the device 178 until the spring loaded rod engages the gear tooth of the detector zero adjustment, and rotating the control knob in the appropriate direction while observing the LED display 158. The oven 64 is also provided with a temperature gauge 180 to provide a visual indication of the temperature within the oven interior for the operator.

Figure 3:
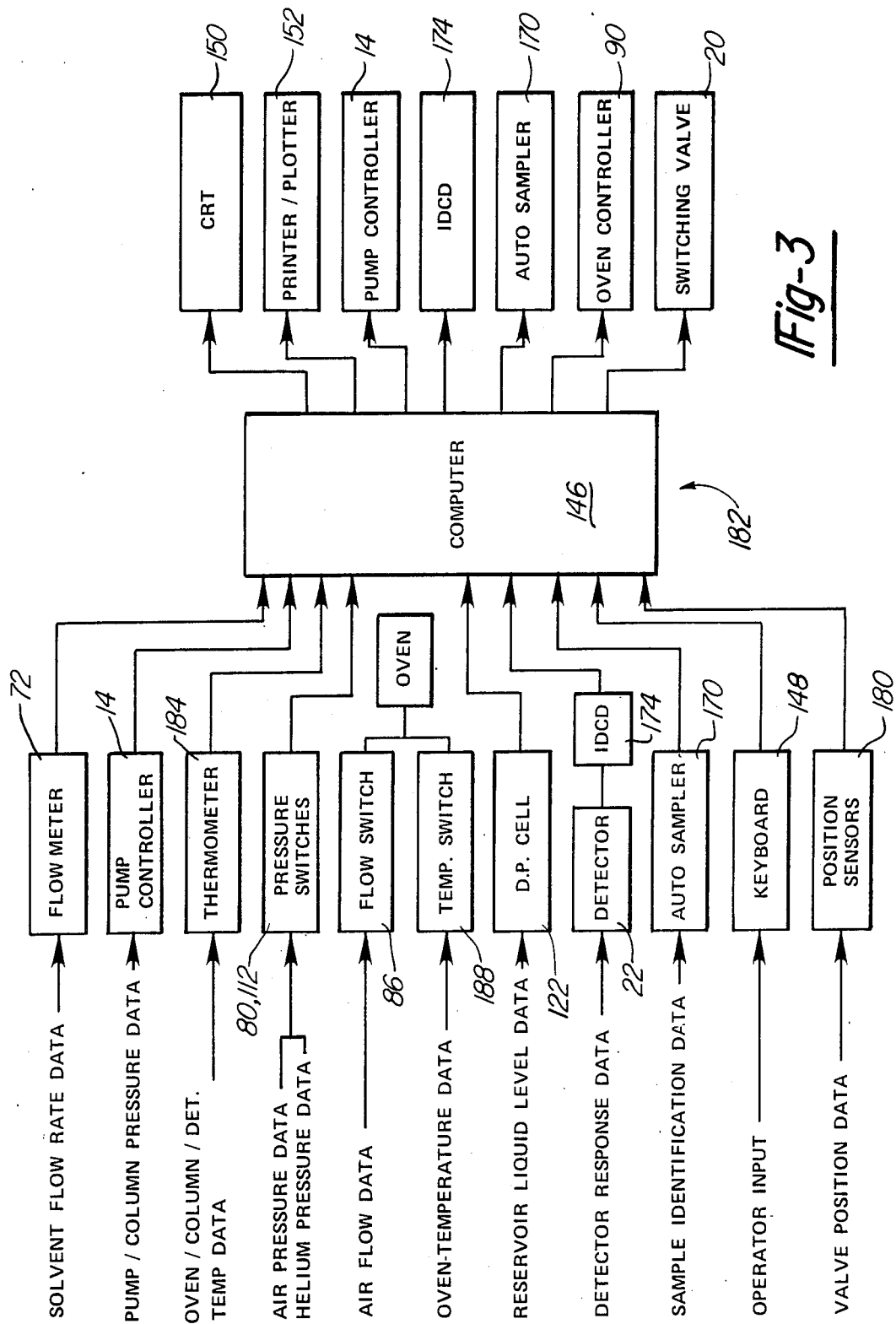
FIG. 3 is a block diagram of the control system for the SEC/GPC chromatograph of FIGS. 1 and 2.

Referring now to FIG. 3, a block diagram from the computer controller 182 for the chromatograph 10 is shown. This block diagram is arranged to show the various input signals to the left of the computer 146, and the various output signals to the right of the computer. For example, the flow meter 42 provides an indication to the computer 146 of the solvent flow rate. Similarly, the pressure transducer 54 illustrated in FIG. 1A provides pump pressure data to the pump controller which forms part of the pump construction 14 in this embodiment. Additionally, the thermistor 184 which senses the temperature of the detector 22 is shown in this figure. A pair of position sensors 186 are provided to detect the position of the switching valve assembly 20 and the injection valve 16.

Each of the input signals illustrated in FIG. 3 are directed to the computer 146 which is provided with conventional interface circuits necessary to receive and process this data. In one form of the present invention, the computer 146 comprises a Digital Equipment Corporation LSI/11 computer which is provided with an ADAC Model 2000 combined CRT/card cage enclosure. Two bubble memory cards (QBI-11/512K) chosen for additional reliablity are used to contain the application and operating system programs for the chromatograph 10. These two bubble memory boards also are used to store the raw data received from the various input signals to the computer 146. Much of the electrical interface between the computer 146 and the various input signals occurs via a DRV11J parallel line interface board. An MLSI-LP11 line printer controller board is also provided as an interface between the computer 146 and the printer/plotter 152.

With respect to the output command signals from the computer 146, these signals include a command signal which turns on and off the pump 14, a command signal which causes the intelligent data collection device 174 to start and stop collecting data, and a command signal to the switching valve assembly 20. A command signal is also provided to the oven controller which energizes the heater 90 in response to a temperature signal from the thermistor 184. It should also be noted that the oven controller receives an air flow signal from the flow switch 86 and an over temperature signal from a thermally actuated switch 188. These signals are used to deactuate the oven heater 90 when the air flow to the oven drops below a predetermined threshold or the temperature in the oven exceeds a predetermined threshold.

Figure 5A:
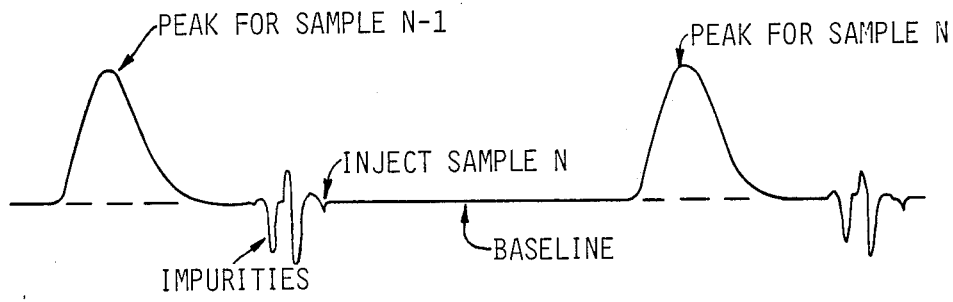
FIGS. 5A–5C are graphical illustrations which relate the molecular weight distribution chromatograph to the sample injection time.

Referring to FIG. 5A, a pair of chromatograms for samples N−1 and N are shown. The vertical axis represents the detector response, while the horizontal axis represents time. The peak curves for both of these samples, as well as the baseline, are all labeled in this figure. Both of these skewed gaussian shape curves are followed by an alternating curve region which is due to the impurities in each of these samples. The point at which the sample N is injected into the chromatograph is illustrated to show that in this figure the sample N is not injected until the sample N−1 has completely eluted from the columns 18. As illustrated in FIG. 5A, there is a significant period of time between the injection of sample N and the beginning of the peak for this sample. While a certain portion of this time is useful in determining the baseline for the sample, a decrease in this period of time is considered desirable, particularly when it is necessary to analyze a number of polymer samples.

Figure 5B:
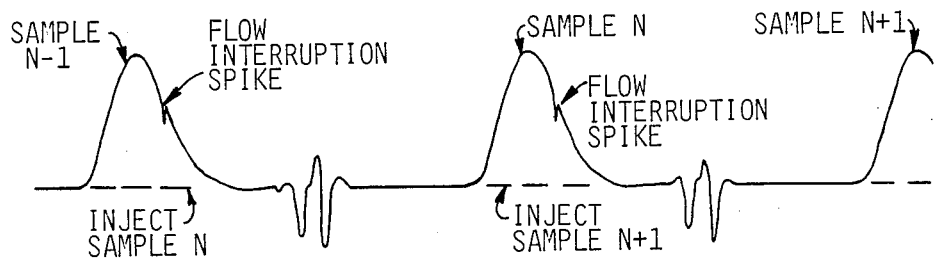
Figure 5C:
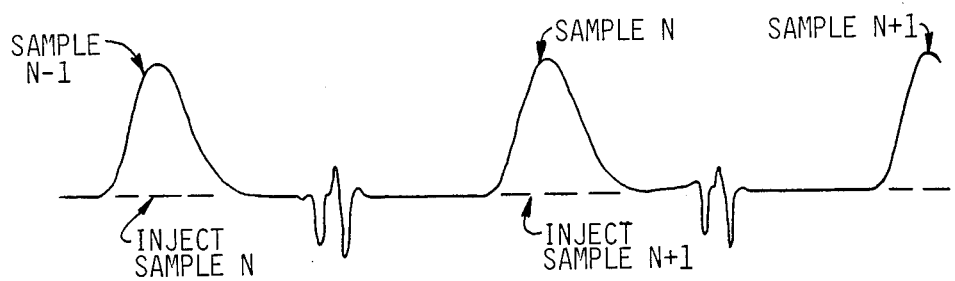

One technique for decreasing the period of time between the injection of two samples would be to inject a sample into the solvent stream before the prior sample has completely eluted from the columns. However, as shown in FIG. 5B, this procedure typically results in a spike or perturbation being produced in the peak signal due to the injection of the next sample in prior SEC/GPC chromatographs. Such a spike or perturbation is undesirable as it will adversely effect the accuracy of the results produced by the chromatograph.

Nevertheless, in accordance with the present invention it is possible to inject a sample into the solvent stream before a prior sample has completely eluted from the columns 18. This is achieved through the provision and control of the rotary sample injection valve 16 which will switch quickly enough so as not to cause a disturbance in the flow of solvent in the flow path to the detector 22. In one form of the present invention, the time period between sample injections can be set to a specific time period (eg., forty minutes) because the type of sample being analyzed will generally be known in the polymer production plant application for the chromatograph.

Figure 6:
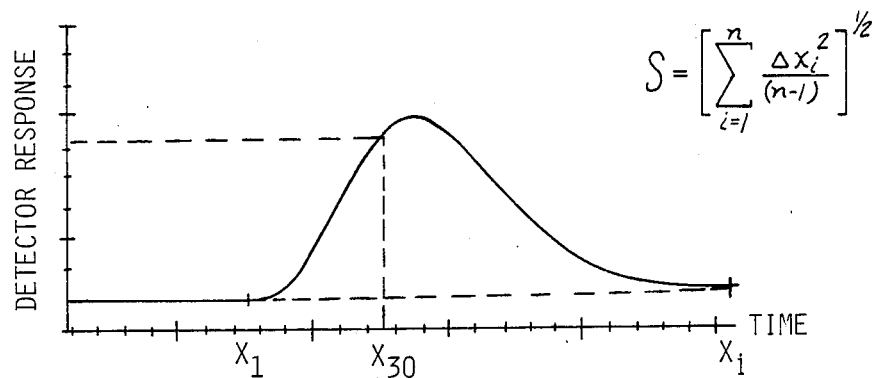
FIG. 6 is a graphical illustration of the molecular weight distribution chromatogram for a broad standard calibration polymer.

Referring to FIG. 6, a chromatogram is shown which illustrates the molecular weight distribution for a particular calibration standard (i.e., Dow Chemical Company's broad molecular weight 1683 polystyrene standard). In accordance with the present invention, a normalized representation of this chromatogram (or other suitable calibration chromatogram) is stored in the memory of the computer 146. Specifically, the chromatogram is divided into a large number of points between the beginning point of the peak ($X_1$) and the ending point of the peak ($X_i$), and the corresponding detector output magnitude is identified, so as to form a table within the memory of the computer of detector output values in terms of time. While it is possible that these molecular weight distribution values could be directly entered into the computer 146, it is preferred that these values be generated and stored by injecting a sample of this calibration standard into the chromatogram 10 for analysis.

The storage in memory of a broad molecular weight distribution standard is advantageous in the chromatograph 10 according to the present invention, because it permits the calibration of the chromatograph to be automatically checked for accuracy. This calibration method involves the injection of the same type of calibration standard into the chromatograph as previously stored in the chromatograph. The chromatograph 10 will then analyze the new calibration standard sample and generate a set of molecular weight distribution values which correspond in time to those previously stored in the computer. These two sets of molecular weight distribution are then compared and the deviation between these sets of values determined by the computer 146 as follows. Assuming that the detector output magnitudes at each of the sample points are represented by $X_i$ (e.g. $X_1$-$X_{100}$), then the difference between each of the corresponding $X_i$ values for the new molecular weight distribution values and the stored molecular weight distribution values may be determined. Then, in accordance with the formula illustrated in FIG. 6, a standard deviation value may then be determined. If this standard deviation value is below a predetermined limit (e.g., 0.05), then the chromatograph 10 is accurately calibrated, and a suitable calibration report to this effect may be generated on the printer/plotter 148. On the other hand, if the standard deviation value is above this predetermined limit, then the computer 146 will generate an error signal which will cause an error message to be printed on the printer/plotter 148. Such an error message could, of course, be also displayed on the CRT 150 if desired.

Additionally, in accordance with the above calibration method, the computer 146 is programmed to calculate the calibration coefficients required to analyze further samples if the chromatograph 10 has been found to be accurately calibrated. One example of a calibration report is set forth below in Table 1.

TABLE I

| Log-Linear Column Calibration: $Log(M_w) = C0 + C1 * t$ | |
|---|---|
| Standard Deviation From 1683 Distribution | 0.0134 |
| Rermissible Limit | 0.0500 |
| Number of iterations | 5 |
| Calibration Coefficients | |
| C0 | 0.105022230E+02 |
| C1 | −0.153032556E+00 |
| Number of iterations to determine C1 | 5 |
| Baseline Limits (minutes after injection) | |
| Low | 27.653 |
| High | 44.653 |
| Area between limits | 6700.48535 |
| Operating Parameters +/− 1 Standard Deviation | |
| Average Pump Pressure (bars) | 30.107 +/− 0.042 |
| Average Oven Temperature (C.) | 39.400 +/− 0.022 |
| Average Detector Temperature (C.) | 39.731 +/− 0.011 |
| Average Pump Flow Rate (ml/min) | 0.994 +/− 0.003 |
| Errors | |
| Minutes | Message |

It should be noted that the calibration report set forth above also provides certain baseline and operating parameter data. For example, the low point in time at which the peak for the sample is indicated in terms of the time following the point at which the sample was injected. Similarly, the high point in time at which the peak for the sample ended is indicated, and the area under the curve between these two limits is provided. Several operating parameters, such as the pump pressure and the oven temperature, are shown. In one form of the present invention, the computer 146 also determines the standard deviation for these operating parameters in order to indicate how stable these parameters were during the period of time between the peak beginning and end points. These standard deviation values can also be used as a basis for automatic decisions.

It should be noted that molecular weight data from the detector 22 is only taken between the beginning and end points of the peak for the sample being analyzed. The computer 146 determines the beginning point of the peak by taking the second derivative of the detector output. When this value as well as the first derivative of the detector output exceeds a predetermined threshold, the computer determines that the peak for the sample has begun. Similarly, the computer determines that the peak has ended by taking the second derivative of the detector output, and determining when this de-acceleration type value drops below a predetermined threshold. Likewise, the point in time at which the peak reaches its maximum height can be determined by the change from a positive to a negative slope for the detector output.

Figure 7A:
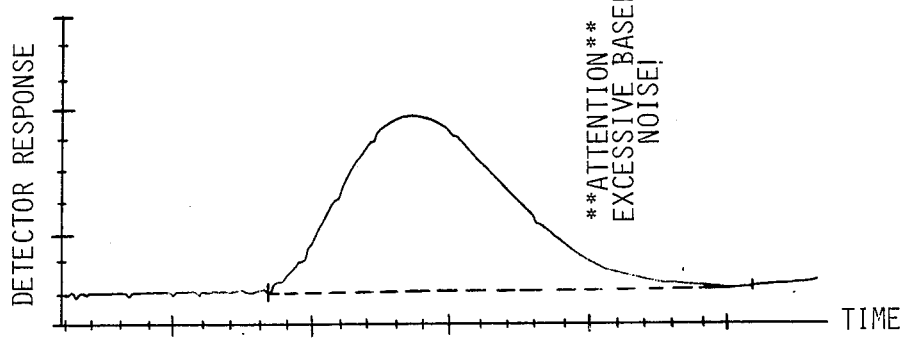
FIGS. 7A–7C are graphical representations which illustrate the chromatograms and error signals which are produced by a SEC/GPC chromatograph according to the present invention in response to the detection of certain error conditions.
Figure 7B:
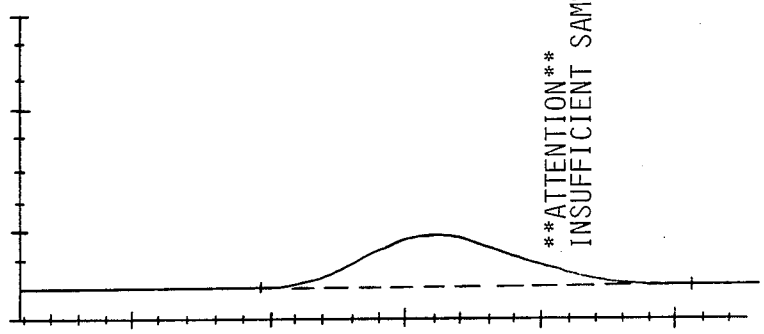
Figure 7C:
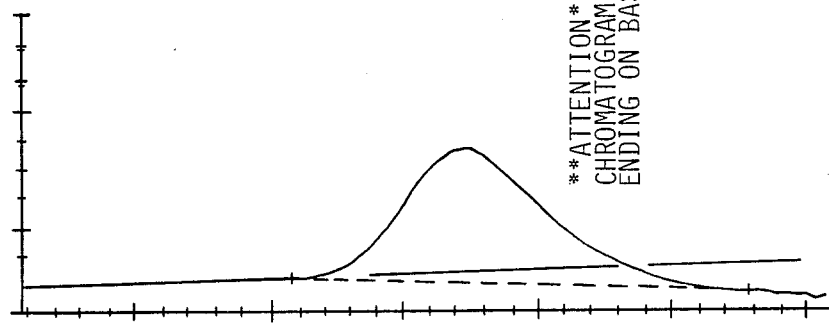

Referring to FIGS. 7A-7C, three chromatograms are shown which represent distinct error conditions which are capable of being self-diagnosed by the chromatograph 10. Specifically, FIG. 7A shows a chromatogram with excessive baseline noise. The computer 146 determined that there is excessive baseline noise by calculating a standard deviation value from a linear least squares fit of the baseline values. If this standard deviation value exceeds a predetermined threshold limit, then the computer 146 will cause the printer/plotter 148 to display an error message in association with the chromatogram plotted by the printer/plotter, as indicated in FIG. 7A. It should be noted that the computer 146 also checks to see if the slope of the baseline is acceptable by finding the equation for the baseline from the detector response as a function of time and determining if the absolute value of the slope in this equation has exceeded a predetermined limit. If the slope is found to be unacceptable for producing accurate results, the computer will cause the printer/plotter to print a similar error message to that shown above in FIG. 7A.

Referring to FIG. 7B, a chromatogram is shown for a condition in which the amount of the sample injected was insufficient to analyze. This error condition is determined by providing a computer program which will determine if the maximum peak height has exceeded a minimum threshold value, and determine if the area under the peak curve has exceeded a minimum area value. If either of these tests fail, the computer 146 will cause the printer/plotter 148 to display an error message as indicated in FIG. 7B.

Turning now to FIG. 7C, a chromatogram is shown for an error condition in which the peak signal did not return to the baseline expected by the computer in accordance with its baseline equation calculated prior to the beginning of the peak for the sample. The dotted line represents the actual baseline extending between the beginning and end points of the peak, while the solid line represents the extrapolated baseline projected by the computer. The computer 146 determines that the peak signal has not returned to the proper baseline by calculating the difference between the magnitude of the detector response for the expected baseline and the actual baseline at the ending point of the peak signal, and checking to see if this difference is greater than a predetermined percentage (e.g., 10 percent) of the maximum peak height (using the expected baseline as a floor). If the chromatogram has not ended sufficiently near to the expected baseline, then the computer 146 will cause the printer/plotter 148 to generate an error message as indicated in FIG. 7C. In all cases, if an error is detected, molecular weight distribution data will not be generated.

Referring to FIGS. 8A-8E, an overall flowchart for the application program of the computer 146 is shown. As indicated by the first block shown in FIG. 8A, the chromatogram 10 begins operation in a shutdown mode. In the shutdown mode, the pump 14 is turned off and the oven heater 90 is also turned off. In this mode, an appropriate menu may be displayed on the CRT 150, and with the appropriate input to the keyboard 148, the operator can initialize the startup for the chromatogram 10. With a commanded start up, the computer 146 will turn the oven heater 90 on, and check to see if the pump 14 is ready. If the pump controller indicates that the pump is not ready, then an error message will be displayed on the CRT 150. Otherwise, the recycle mode will be initiated. In the recycle mode, the computer will command that the position of the switching valve assembly 20 be changed. Then, a check will be made to see if the switching valve assembly 20 is in the recycle position. If so, then the operator will preferably wait a relatively extended period of time (e.g., 24 hours) for the system to reach an equilibrium condition.

When the operator determines that the equilibrium condition has been reached, then a dump mode can be initiated through the appropriate keyboard entry. In the dump mode, the computer will cause the switching valve assembly to switch the solvent flow to the analytical side of the detector 22. A check will then be made to see if the solvent liquid level in the reservoir 12 is above a predetermined threshold. If the solvent level is below this threshold, the computer will cause a return to the recycle mode by changing the position of the switching valve assembly 20. An error message will then be displayed on the CRT 150 as a prompt to the operator that it is time to replenish supply of solvent in the reservoir 12.

Figure 8A:
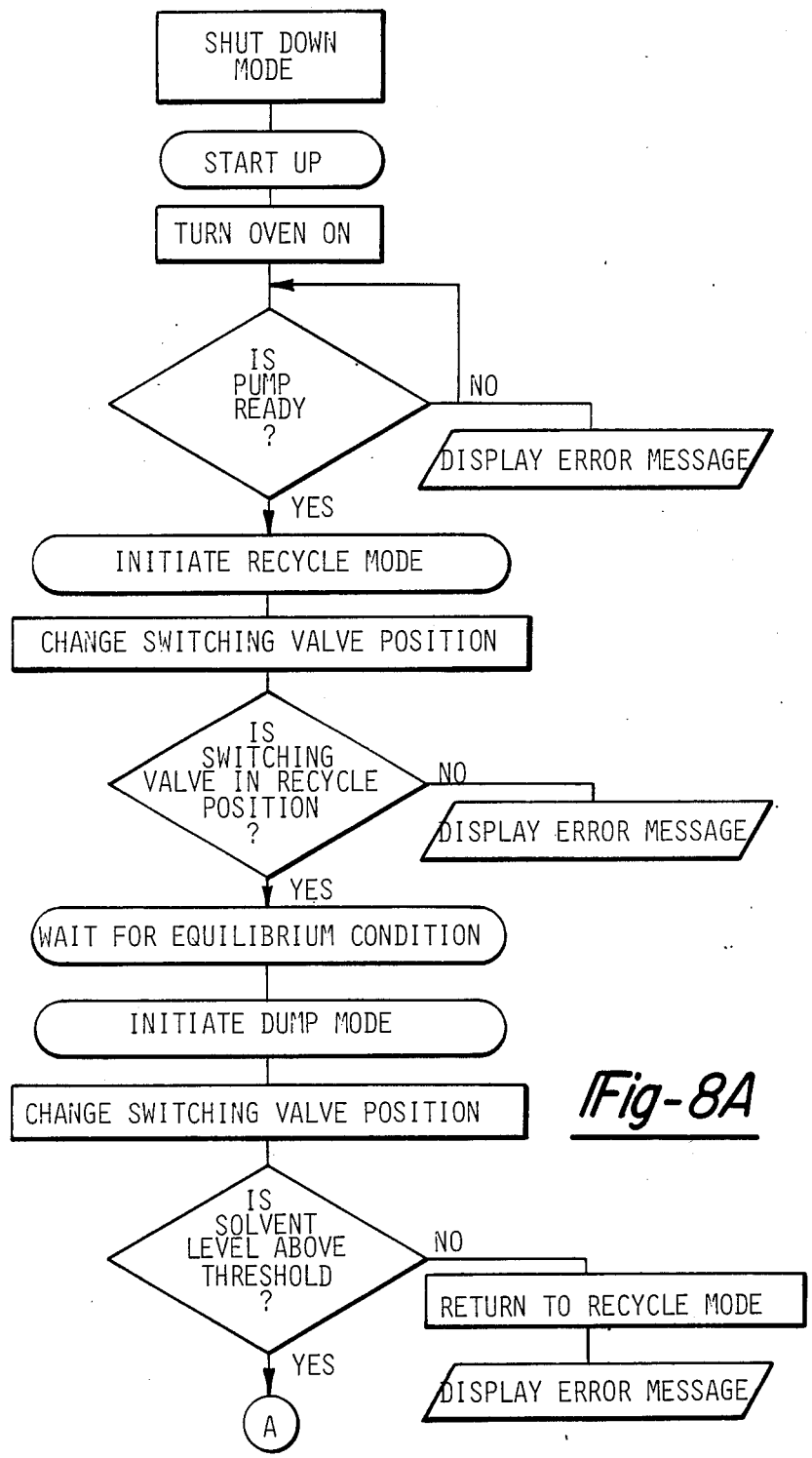
FIGS. 8A–8E illustrate an overall flow chart for the chromatograph computer controller and method according to the present invention.
Figure 8B:
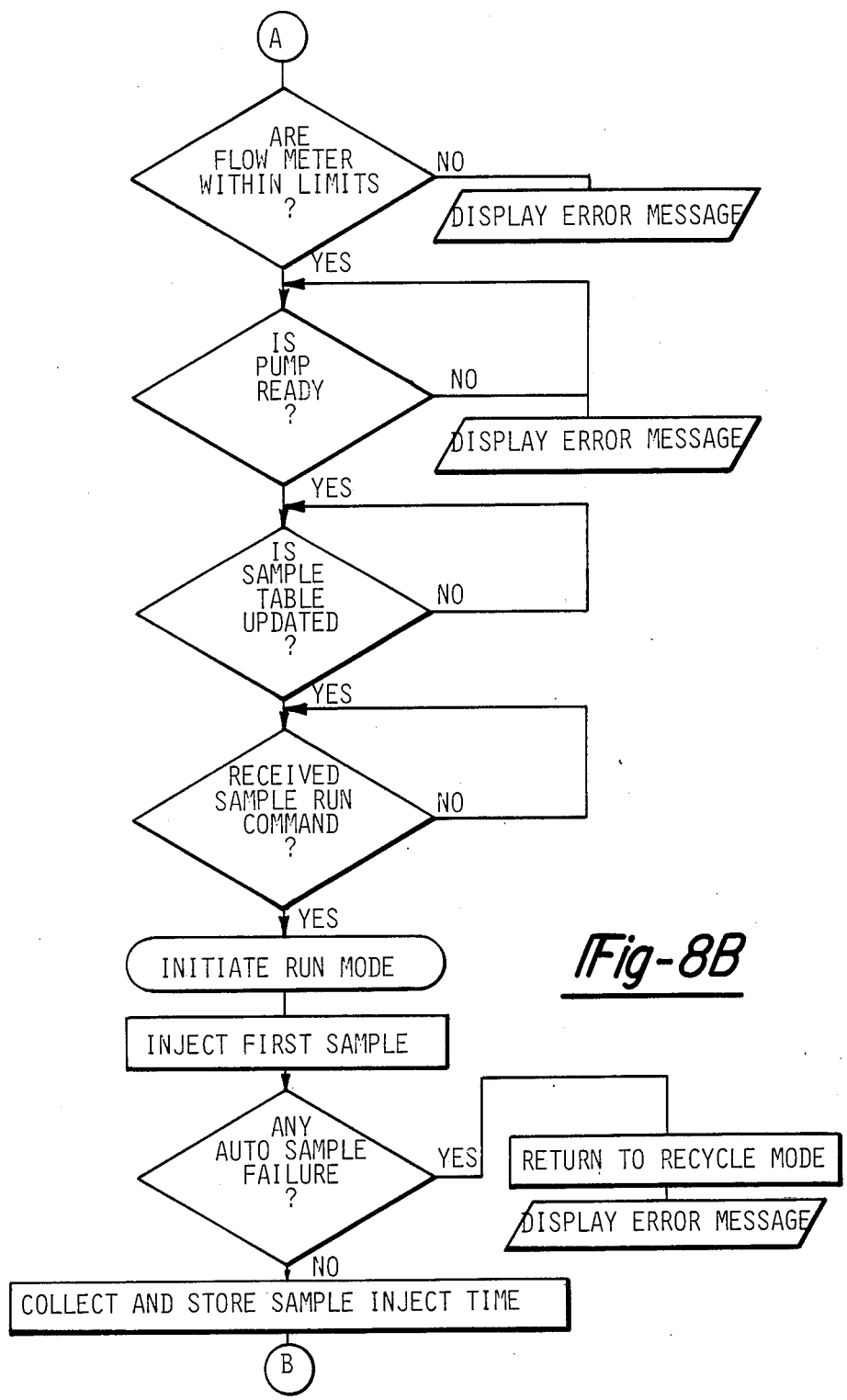

Continuing in FIG. 8B, the computer runs several checks before permitting any samples to be injected into the chromatograph 10. Specifically, the computer checks to see if the flow meters (e.g., the solvent flow meter 72) are within limits. The pump is again checked to assure that it is in a ready condition. The computer also checks to see if the operator has identified each of the samples to be analyzed in a sample table which can be updated via the keyboard 148. The computer then waits to receive a sample run command from the operator via the keyboard 148.

When the sample run command is received, the computer 146 will initiate a run mode, and cause the sample changer assembly 126 to inject the first sample into the solvent stream. The computer will then interrogate the control module 170 for the sample changer to determine if there has been any sample failure, such as the failure to find a sample vial 128 in the carousel for the sample changer. If there has been a sample failure, the computer will cause the position of the switching valve assembly to be changed back to the recycle mode. If there have been no sample inject failures, then the computer will collect and store the time at which the sample was injected.

Figure 8C:
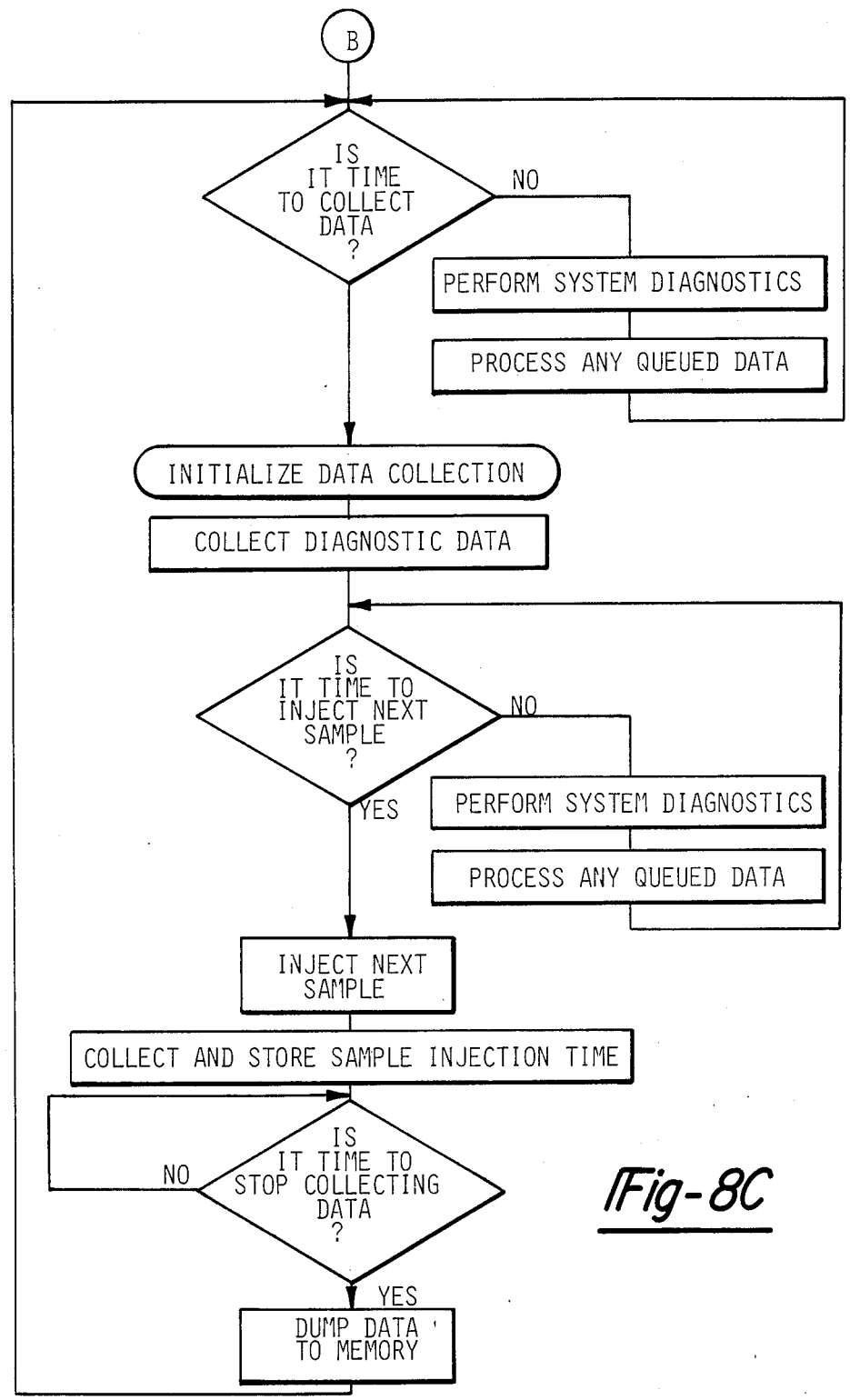

As shown in FIG. 8C, the computer will continually check to see if it is time to begin collecting data from the detector 22. If sufficient time is not yet passed, the computer will preferably perform various system diagnostics, such as determining if the flow rates, temperatures, and pressures are all within certain predetermined limits. Then, the computer will process any cueued data which has not already been processed, such as the data from a previous sample.

If it is time to start collecting data, such as prior to the sample eluant, then the computer 146 will initialize the data collection by commanding the intelligent data collection device 174 to begin collecting data. At this time, the computer will also continue to collect diagnostic data, such as flow rates, temperatures, and pressures. Since it is desirable in accordance with the present invention to inject the next sample before the first prior sample has completely eluted from the columns 18, the computer will next check to see if it is time to inject the next sample. If not, the computer will continue to perform system diagnostics and process any cueued data. If yes, then the computer will command the sample changer assembly 126 to inject the next sample. This sample injection time will then be collected and stored.

At this point, the computer will check to see if it is time to stop collecting detector response data from the first sample. When it is time to stop collecting data, the computer will command that the intelligent data collection device 174 dump its detector response data to the bubble memory in the computer. At this point, the computer program will jump back to the beginning diamond shown in FIG. 8C to check if it is time to start collecting data for the second or subsequent sample which has been injected.

Figure 8D:
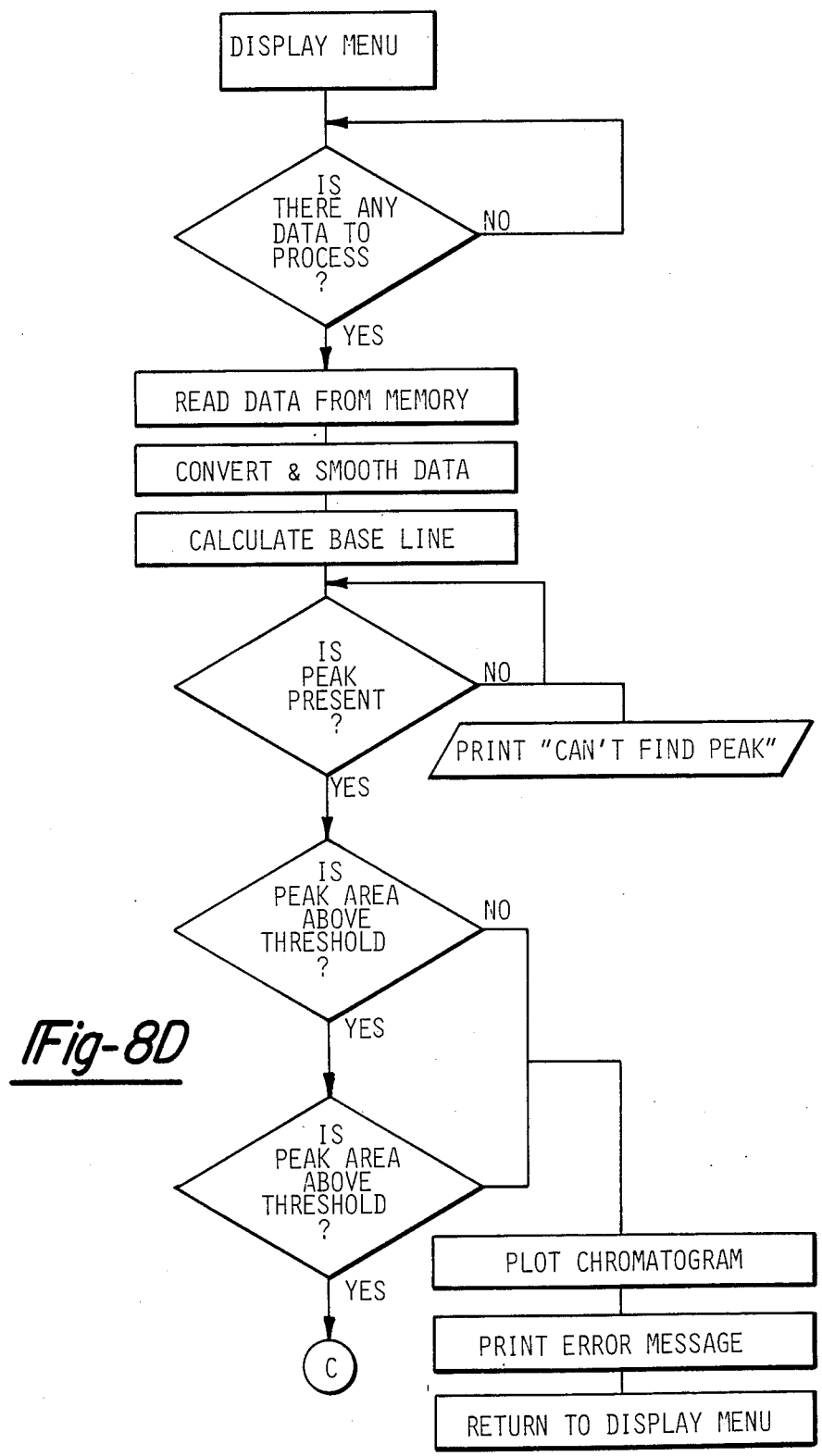

Referring to FIG. 8D, the background portion of the computer program will determine if there is any data to process. At this time, a menu will be displayed on the CRT 150 which will enable the operate to change the particular operating mode of the chromatograph 10. If there is any data to process, the computer will read this data from memory, convert the data from ASCII to binary form, and smooth the data by averaging.

The computer will then calculate the baseline equation from the detector response before the arrival of the peak for the sample. Following this, the computer will continue checking to find the beginning of the peak for the sample. If the peak cannot be found after a predetermined amount of time, the computer will cause the printer/plotter to print a suitable error message as shown in FIG. 8D.

If the peak has been found by the computer, the computer will then perform the various self-diagnostic tests described above. Thus, the computer will determine if the peak height is above a minimum predetermined threshold, and if the peak area is above a minimum predetermined threshold. If the detector response is found to be unacceptable, then the computer will cause the printer/plotter 148 to plot the chromatogram, and print a suitable error message.

Figure 8E:
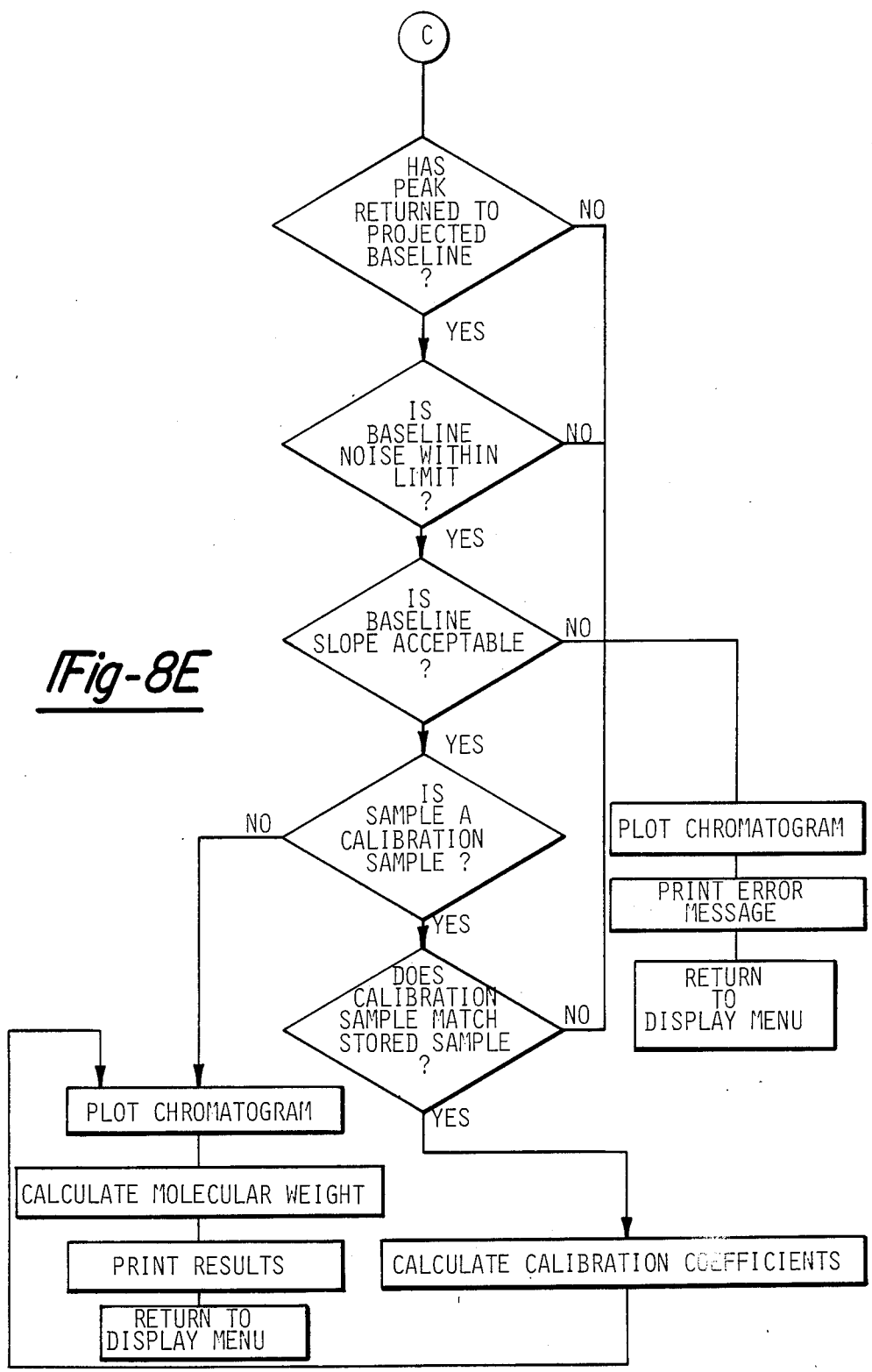

Continuing in FIG. 8E, the computer will check to see if the peak for the sample has returned to the projected baseline, and check to see if the noise and slope for the baseline are within acceptable limits. Assuming that the detector response data has passed the tests above, the computer will then check the sample table to determine if the sample is a calibration standard or an unknown. If the sample is found to be a calibration standard, the compound will check to see if the deviation between the molecular weight distribution values for this sample and the stored molecular weight distribution values have exceeded a predetermined threshold. If the calibration is found to be acceptable, the computer will then calculate the calibration coefficients needed to calculate the molecular weight distribution for the unknown samples to be analyzed. Finally, the computer will cause the printer/plotter to plot the chromatogram for the calibration standard or the unknown. The computer will also calculate the molecular weight distribution and cause the results of the analysis to be printed on the printer/plotter.

It should also be noted that if the computer 146 detects a pump or air pressure failure, the computer will cause the chromatograph 10 to the controlled shutdown mode. However, if the computer detects a decrease in the helium gas pressure below a predetermined limit, the computer will command the switching valve 20 to revert back to the recycle position.

It will be appreciated that the above disclosed embodiments is well calculated to achieve the aforementioned objectives of the present invention. In addition, it is evident that those skilled in the art once given the benefit of the foregoing disclosure, may now make modification to this specific embodiment described herein without departing from the spirit of the present invention. Such modifications are to be considered within the scope of the present invention which is limited solely by the scope and spirit of the appended claims.

We claim:

1. A diagnostic SEC/GPC chromatograph for determining the molecular weight distributed of polymer samples, comprising:
   column means for fractionating polymer samples by molecular weight;
   conveying means for causing a stream of solvent to flow through said column means from a source of said solvent;
   injection valve means for injecting a polymer sample into said solvent stream of said conveying means before said column means;
   detector means connected to said conveying means at the output of said column means for generating a peak signal indicative of the molecular weight of the fractionated polymer sample eluting from said column means;
   controller means for processing said peak signal from said detector means into molecular weight distribution values, said controller means including first processor means for determining a baseline from said peak signal, second processor means for determining if the slope of said baseline is within predetermined limits, and third processor means for determining if said peak signal returns to said baseline, said controller means generating an error signal in response to any unacceptable diagnostic determinations of said processor means, said unacceptable diagnostic determinations including said baseline slope being outside of said predetermined limits and said peak signal not returning to said baseline; and
   output means for producing a visually perceptible indication of said molecular weight distribution values and an error message in response to the presence of said error signal.

2. The chromatograph according to claim 1, wherein said controller means including fourth processing means for determining if the presence of noise in said baseline exceeds a predetermined limit.

3. The chromatograph according to claim 1, wherein said controller means includes fourth processing means for determining if the magnitude of said peak signal exceeds a predetermined threshold level.

4. The chromatograph according to claim 1, wherein said controller means includes fourth processing means for determining if the area between said baseline and the portion of said peak signal above said baseline exceeds a predetermined threshold level.

5. The chromatograph according to claim 1, wherein said chromatograph includes sensor means for detecting the flow rate of said solvent, and said controller means includes processor means for determining if said solvent flow rate is within predetermined limits.

6. The chromatograph according to claim 1, wherein said output means is a printer/plotter.

7. A SEC/GPC chromatograph for determining the molecular weight distribution of polymer samples, comprising:
   column means for fractionating polymer samples by molecular weight;
   conveying means for causing a stream of solvent to flow through said column means from a source of said solvent;
   rotary injection valve means for sequentially injecting a series of polymer samples into said solvent stream of said conveying means before said column means;
   detector means connected to said conveying means at the output of said column means for generating a peak signal indicative of the molecular weight of the fractionated polymer samples eluting from said column means; and
   controller means for processing said peak signal from said detector means into a molecular weight distribution output and for controlling said valve means such that a subsequent polymer sample is injected into said solvent stream before a prior polymer sample has completely eluted from said column means without interrupting the flow of said solvent stream.

8. A SEC/GPC chromatograph for determining the molecular weight distribution of polymer samples, comprising:
   reservoir means for containing a supply of a solvent;

column means for fractionating polymer samples by molecular weight;

first conveying means for causing a stream of solvent to flow from said reservoir means and through said column means;

first valve means for injecting a polymer sample into said solvent stream of said first conveying means before said column means;

detector means for generating a peak signal indicative of the molecular weight of the fractionated polymer sample eluting from said column means;

second valve means interposed between said column means and said detector means for selectively diverting the flow of said solvent between the reference and analytical sides of said detector means;

second conveying means for permitting solvent to flow from the reference side of said detector means to said reservoir means; and controller means for processing said peak signal into a molecular weight distribution output, and for controlling said second valve means such that a recycle mode is provided when said second valve means causes solvent to flow through the reference side of said detector means and back to said reservoir means, and a run mode is provided when said valve means causes solvent to flow through the analytical side of said detector means.

9. The chromatograph according to claim 8, including sensor means for generating a signal indicative of the solvent liquid level in said reservoir means, and wherein said controller means includes processor means which determines whether the solvent liquid level is below a predetermined threshold and causes said controller means to switch said second valve means to the recycle mode if said solvent liquid level is below said predetermined threshold and said second valve means is in the run mode.

10. The chromatograph according to claim 9, wherein said sensor means comprises a differential pressure cell connected to a source of helium gas for measuring the back pressure on said helium gas caused by the solvent liquid level in said reservoir means.

11. The chromatograph according to claim 8, wherein said reservoir means comprises a container having outlet port means for permitting the discharge of solvent from said container above a predetermined threshold level.

12. The chromatograph according to claim 8, including third conveying means for selectively causing solvent to flow to said reservoir means from a source of said solvent.

13. The chromatograph according to claim 8, including oven means for controlling the temperature of said column means and said detector means, and manually adjustable actuator means mounted through the door of said oven means for adjusting the baseline sensitivity of said detector means.

14. A method of calibrating a SEC/GPC chromatograph and determining the molecular weight distribution of polymer samples, comprising the steps of:

(a) storing the molecular weight distribution values for a predetermined calibration polymer standard;

(b) injecting a sample of said polymer standard into a solvent stream;

(c) conveying said polymer standard through at least one column for fractionating polymers by molecular weight;

(d) conveying said fractionated polymer standard through a detector which generates a peak signal indicative the molecular weight of said fractionated polymer standard as it elutes from said column;

(e) processing said peak signal into measured molecular weight distribution values;

(f) comparing said measured and stored molecular weight distribution values and determining the difference between these values;

(g) producing calibration coefficient values when the difference between said measured and stored molecular weight distribution values is below a predetermined deviation value; and (h) generating a physically perceptible output indicative of a calibration error when the difference between said measured and stored molecular weight distribution values exceeds said predetermined deviation value.

15. The method according to claim 14, further including the steps of:

(i) injecting a polymer sample to be analyzed in said solvent stream;

(j) conveying said polymer sample through said column and said detector;

(k) processing said peak signal into molecular weight distribution values by utilizing said calibration coefficients; and (l) generating a physically perceptible output indicative of the molecular weight distribution for said polymer sample from said molecular weight distribution values.

* * * * *